United States Patent [19]

Meszaros et al.

[11] Patent Number: 5,393,661
[45] Date of Patent: Feb. 28, 1995

[54] THREE REAGENT GRAM STAINING METHOD AND KIT

[75] Inventors: Amy T. Meszaros, Adrian; Leon F. Strenkoski, Dexter, both of Mich.

[73] Assignee: Difco Laboratories, Ann Arbor, Mich.

[21] Appl. No.: 172,416

[22] Filed: Dec. 22, 1993

[51] Int. Cl.⁶ .............................................. C12Q 1/04
[52] U.S. Cl. ......................................... 435/34; 435/4; 435/29; 435/810; 424/3; 8/94.11
[58] Field of Search ...................... 435/34, 4, 29, 810; 424/3; 8/94.11

[56] References Cited

U.S. PATENT DOCUMENTS

| | | | |
|---|---|---|---|
| 4,225,669 | 9/1980 | Melnick et al. | 435/29 |
| 4,857,459 | 8/1989 | Reuben | 435/34 |
| 4,916,061 | 4/1990 | Di Ianni | 435/34 |

OTHER PUBLICATIONS

Romero et al., *J. Clin. Microbiol*, vol. 26, No. 7, pp. 1378–1382, Jul. 1988.
Wallis et al., *Biological Abstract*, vol. 73, No. 3, Ref. No. 18314, 1981 (J. Clin. Microbiol. 14(3) 342–346, 1981).

*Primary Examiner*—Michael G. Wityshyn
*Assistant Examiner*—Abdel A. Mohamed
*Attorney, Agent, or Firm*—Reising, Ethington, Barnard, Perry & Milton

[57] ABSTRACT

A method for Gram staining a specimen containing bacteria includes the steps of staining Gram positive bacteria in the specimen, fixing the stain to the Gram positive bacteria, and simultaneously decolorizing and counter-staining Gram negative bacteria in the specimen.

42 Claims, 1 Drawing Sheet

THREE REAGENT GRAM STAINING METHOD AND KIT

TECHNICAL FIELD

The present invention relates to a reagent and a staining method for bacteria. More particularly, the present invention relates to a Gram staining reagent combining a decolorizer and a counter-stain and a three reagent Gram staining method.

BACKGROUND ART

The Gram stain is a well known and widely used microbiological technique used for classifying and identifying bacteria. In hospitals and clinical laboratories, the Gram stain is one of the most frequently performed microbiological diagnostic tests. The Gram stain essentially divides the bacterial world into two distinct classifications: Gram positive bacteria and Gram negative bacteria. Separation into these two classes is based on differences in the structure of the bacterial walls.

The conventional and most commonly used method of the Gram staining technique requires the use of four separate reagents. The reagents consist of a primary staining solution usually containing crystal violet dye, a mordant solution usually containing an iodine-potassium iodide solution, a decolorizing agent usually a solution of acetone and alcohol, and a counter-staining solution usually containing safranin. The conventional method involves the steps of: (1) treating a slide having bacteria affixed upon it with the principal stain, waiting 30–60 seconds; (2) rinsing the slide with water; (3) treating the slide with the mordant solution, waiting 30–60 seconds; (4) rinsing slide with water; (5) decolorizing the slide with acetone and alcohol solution, waiting 30–60 seconds; (6) rinsing the slide with water; (7) counter-staining the slide with the safranin or fuchsin solution for 30–60 seconds and; (8) rinsing the slide with water. Only after these steps are completed can the bacteria affixed to the slide be observed and analyzed to determine Gram status. Typically, Gram positive bacteria will appear purple in color, while Gram negative bacteria will appear reddish, pink in color.

It should be obvious, from the above description of the conventional method of Gram staining, that the conventional method of Gram staining is a very involved, time consuming, and labor intensive process. Each additional step introduces the possibility of error which can lead to an incorrect or inconclusive identification of the bacteria. A Gram stain which results in an inconclusive or incorrect identification of a bacterial specimen must either be repeated or have other diagnostic tests performed to more positively identify the bacterial specimen. In either case, the initiation of effective treatment is delayed when conclusive bacterial identification is not obtained.

For years, technicians using the conventional Gram staining method have been plagued by these inconsistent results. Much of the inconsistency is directly attributable to the conventional method itself. For instance, the separate decolorizing step is problematic in that it is difficult to achieve the proper amount of decolorization of the bacteria. In other words, decolorization, the step of removing the fixed crystal violet stain from the Gram negative organisms, is prone to inconsistency. The inconsistency stems from difficulties associated with the amount of decolorizing solvent applied to bacteria and the amount of time the decolorizing solvent is allowed to contact the bacteria. If the decolorizing solvent is applied in large volumes or is applied too vigorously, the bacteria in the sample may be under-stained, thereby potentially yielding an inconsistent or incorrect result i.e., a truly Gram positive bacterium may appear to be a Gram negative bacterium. If, on the other hand, a bacterial sample is not adequately decolorized, the bacteria in the sample may be over-stained, thereby potentially yielding an inconsistent or incorrect result i.e., truly Gram negative bacterium may appear to be a Gram positive bacterium.

Using the conventional four reagent Gram staining method, certain bacteria may appear as to be both Gram positive and Gram negative. These bacteria are referred to in the art as Gram variable bacteria. Gram variable bacteria present a unique challenge to the technician in that the results of a Gram stain on a pure culture of one of these bacteria could yield both Gram positive and Gram negative bacteria or the bacteria may be stained in such a way that it is impossible to make a determination of the bacteria's Gram status. Instead of Gram positive bacteria appearing purple in color and Gram negative bacteria appearing reddish, pink in color, the bacteria may appear brownish purple or simply just brown. A result like this makes identifying and classifying a bacterial sample very difficult, as is described below.

In addition to inconsistency, the conventional Gram staining method takes more time to perform i.e., an additional reagent adds at least another one minute application period and an additional water wash. Also, the conventional Gram staining method is more costly, since costs typically increases the more reagents that are involved and there is a cost associated with a technician or a machine performing the additional manipulations connected with an additional reagent.

U.S. Pat. No. 4,857,459 to Reuben discloses a method for staining acid-fast bacilli which utilizes a decolorizing counter-stain solution containing methylene blue, ethyl alcohol, potassium hydroxide, glycerol, acetic acid, and polyvinylpyrollidone. However, the decolorizing counter-stain solution and method for its use disclosed in the Reuben '459 patent are for performing an acid-fast stain and not for performing a Gram stain.

There have been other attempts to streamline the conventional Gram staining method and reagents. U.S Pat. No. 4,916,061 to Di Ianni discloses a Gram staining method in which the number of individual reagents was reduced by combining the mordant and the decolorizer into a single reagent comprised of an iodine-iodide salt complex and an alcohol solvent. The Di Ianni '061 patent sought to both streamline the Gram staining process and also to provide a more stable, longer lasting mordant solution. Unfortunately, this method provides inadequate results and, therefore, has no real utility, as described in detail below. It, therefore, follows that simply combining reagents from the conventional Gram staining method does not necessarily yield an improved method or unexpected results. Additionally, merely combining the counter-stain and the decolorizer without adjusting the pH to approximately 4.5 does not provide a pronounced improvement over prior art Gram staining methods.

The present invention not only streamlines the Gram staining method, it yields the added benefits of improved accuracy and performance by eliminating the certain long standing problems such as over/under decolorizing and variability.

SUMMARY OF THE INVENTION

A method according to the present invention for Gram staining a specimen containing bacteria and other cells includes the steps of staining Gram positive bacteria in the specimen, fixing the stain to the Gram positive bacteria, and simultaneously decolorizing and counter-staining Gram negative bacteria in the specimen.

BRIEF DESCRIPTION OF THE DRAWINGS

The file of this patent contains at least one drawing executed in color. Copies of this patent with color drawing(s) will be provided by the Patent and Trademark Office upon request and payment of necessary fee.

Other advantages of the present invention will be readily appreciated as the same becomes better understood by reference to the following detailed description when considered in connection with the accompanying drawings wherein.

DETAILED DESCRIPTION OF THE INVENTION AND ADVANTAGES

Figure 1:
FIG. 1 is a photograph of *Bacillus megaterium* ATCC 14581, a Gram positive organism, which has been Gram stained using the traditional four step method.

The present invention provides a method for Gram staining a specimen containing bacteria and other cells. Prior to commencing the subject Gram staining method, a bacterial sample is first obtained and affixed to a support structure. The bacteria can be obtained from any suitable source such as a pure culture, a wound exudate, a blood smear, a sputum sample or the like. The bacteria are affixed to the support structure which can be a standard glass microscope slide by heating, alcohol treatment or other suitable means of fixation as are known in the art.

The first step in the subject method is staining the bacteria affixed on the slide with a reagent solution containing a primary dye capable of staining Gram positive bacteria. Crystal violet, or as it is sometimes referred to as gentian violet, is the preferred primary dye for staining Gram positive bacteria. The crystal violet dye is dissolved in a solvent which is typically water or an alcohol such as ethanol or isopropanol. The crystal violet solution may also include certain other minor components such as phenol or aniline which are added to increase the solubility and stability of the crystal violet in the solution. Staining the bacteria affixed to the slide includes applying the crystal violet solution the bacteria affixed to the slide using any suitable means such as a squeeze bottle, an eye dropper, or any other suitable means for applying a solution. The staining step also includes an application period in which the crystal violet solution is allowed to incubate or contact the bacteria for a period of time, typically one minute. Following the application period, the bacteria affixed to the slide are gently washed with water to remove any excess crystal violet solution.

Following the staining step, a mordant solution is applied to the bacteria in order to fix the primary dye within the bacteria. The mordant solution forms insoluble compounds with the primary dye, that is, the crystal violet dye present within the bacteria is altered so that it will only be retained by Gram positive bacteria. The mordant solution typically comprises an iodine-iodide salt complex dissolved in a solvent, such as water. The iodine comprising the iodine-iodide salt complex is generally crystallized iodine. The iodide salt can be any number of different iodide salts but is generally one of either potassium iodide, sodium iodide, magnesium iodide, aluminum iodide, zinc iodide, and ferrous iodide. Additionally, the mordant solution can comprise iodine complexed with polyvinylpyrrolidone. The mordant solution may also be comprised of an iodine concentrate/diluent preparation. The iodine concentrate/diluent preparation would provide a more stable means for transport and add to the shelf life of the solution.

Fixing the crystal violet dye within the Gram positive bacteria is accomplished by applying the mordant solution to the bacteria affixed to the slide using any suitable means such as a squeeze bottle, an eye dropper, or any other suitable means for applying a solution. The fixing step also includes an application period in which the mordant solution is allowed to incubate or contact the bacteria for a period of time, typically one minute.

Following the application period, the bacteria which were affixed to the slide and previously treated with the mordant solution are gently washed with a combination decolorizing and counter-staining solution to remove any excess mordant solution. This final step in the subject Gram staining method simultaneously decolorizes and counter-stains the previously treated bacteria affixed to the slide. The step of simultaneously decolorizing and counter-staining the bacteria affixed to the slide allows for removal of any fixed crystal violet dye from Gram negative bacteria (decolorization) which, because of the structure of their bacterial walls, do not retain fixed crystal violet dye and, at the same time, stains the bacteria with a second dye capable of staining Gram negative bacteria (counter-staining). In the final step of the subject method, a counter-stain is applied to the bacteria to stain the Gram negative with a differentiating stain to allow the Gram negative bacteria to be identified. In other words, a solution is applied to the bacteria which removes fixed crystal violet dye from any Gram negative bacteria present in bacterial specimen while, simultaneously, introducing a second stain into those same Gram negative bacteria to allow for the differentiation of Gram positive and Gram negative bacteria.

The step of simultaneously decolorizing and counter-staining Gram negative bacteria is accomplished by applying the combination decolorizing and counter-staining solution to the bacteria affixed to the slide. The combination decolorizing and counter-staining solution includes a solvent for removing the fixed crystal violet dye from Gram negative bacteria, a counter-stain for staining Gram negative bacteria, and a buffer solution.

In the preferred embodiment the solvent is ethanol, but may be methanol, isopropanol, chloroform, or acetone. Additionally, water may be included in the solvent in concentrations ranging from about 0% to 25%, and preferably is about 10%.

The combination decolorizing and counter-staining reagent solution also includes a stain capable of staining Gram negative bacteria. In the preferred embodiment, the counter-stain is safranin, but fuchsin or any other suitable dye may be substituted. The concentration of safranin in the reagent solution for simultaneously decolorizing and counter-staining the Gram negative bacteria can range from about 0.25% to 0.8%. The preferred concentration of safranin is about 0.4%. The concentration of ethanol in the reagent solution for simultaneously decolorizing and counter-staining the Gram negative bacteria can range from about 75% to 100%, and preferably is about 90%.

The buffer in the combination decolorizing and counter-staining solution may be any number of different buffering agents but is generally acetate, TRIS, or other suitable buffers known to those skilled in the art. Many buffers may be suitable as long as they are soluble in the solution and possess similar buffering capacity in the preferred pH range. The preferred buffer is an acetate buffer ranging in concentration from 0.01M to 1M. The preferred concentration of acetate buffer is 0.1M. Buffering the combination decolorizing and counter-staining solution is crucial for staining mammalian cells present in specimens to be analyzed.

In addition to the constituents which comprise the combination decolorizing and counter-staining solution, the pH of the solution is also critical to the present invention. The optimal pH range for the combination decolorizing and counter-staining solution is in the acidic range between pH=1 to pH=6. The preferred pH for the solution is approximately pH=4.5. Acidification is critical in order to resolve and differentiate mammalian cells which may be present in a clinical specimen. Without adjusting the pH of the combination decolorizing and counter-staining solution within this range, mammalian cells such as polymorphonuclear leukocytes (PMN's), mononuclear cells, epithelial cells and similar type cells are difficult to distinguish and resolve from a Gram stained bacterial slide. These other cells can be a valuable aid in diagnosis and bacterial typing since they are important indicators of inflammation and specimen quality.

The simultaneous decolorizing and counter-staining step is accomplished by applying the combination decolorizing and counter-staining solution to the bacteria affixed to the slide using any suitable means such as a squeeze bottle, an eye dropper, or any other suitable means for applying a solution. The simultaneous decolorizing and counter-staining step also includes an application period in which the combination decolorizing and counter-staining solution is allowed to incubate or contact the bacteria for a period of time, typically 20–40 seconds. Following the application period, the bacteria affixed to the slide are gently washed with water to remove any excess decolorizing and counter-staining solution. At this point, the bacteria affixed to the slide are in a condition suitable for microscopic analysis to determine if the bacteria are Gram positive, Gram negative, or a combination of both.

The present invention also includes a kit containing the Gram staining reagents including a first reagent means for staining Gram positive bacteria; a second reagent means for fixing the stain to the Gram positive bacteria; and a third reagent means comprised of a solvent, a counter-stain, and a buffer for simultaneously decolorizing and counter-staining Gram negative bacteria, all of which are as previously described above.

EXAMPLES

Example 1

Materials and Methods

Samples of microorganisms including bacterial and yeast specimens (see Table 1) were affixed to glass microscope slides and were treated with conventional four reagent Gram staining method comprised of an aqueous principal staining solution containing 0.38% crystal violet, 0.44% phenol; a mordant solution containing 0.33% iodine crystals, 0.66% potassium iodide; a decolorizing solution containing acetone and isopropanol in a ratio of 1:3, respectively; and a counter-staining solution containing 0.4% safranin and 20% ethanol.

Using the conventional Gram staining method the microorganisms were: (1) treated with the principal staining solution for 30–60 seconds; (2) rinsed with water; (3) treated with the mordant solution for 30–60 seconds; (4) rinsed with water; (5) treated with the decolorizing solution for 30–60 seconds; (6) rinsed with water; (7) treated with the counter-staining solution for 30–60 seconds and; (8) rinsed with water. Following these steps, the microorganisms were microscopically analyzed and the results are shown in Table 1.

For the three reagent method of the present invention, identical microorganism samples including bacterial and yeast specimens were affixed to glass microscope slides and were treated with a principal staining solution containing 0.38% crystal violet, 0.44% phenol; a mordant solution containing 10% polyvinylpyrolidone-iodine crystals, 0.66% potassium iodide; and a combination decolorizing and counter-staining solution containing 0.40% safranin, 90% ethanol, and 10% water in a 0.1M acetate buffer, pH 4.5.

Using the three reagent Gram staining method of the present invention, the microorganism samples were: (1) treated with the principal staining solution for 30–60 seconds; (2) rinsed with water; (3) treated with the mordant solution for 30–60 seconds; (4) rinsed with the combination decolorizing and counter-staining solution; (5) treated with the combination decolorizing and counter-staining solution for 20–40 seconds; (6) rinsed with water. Following these steps, the microorganism samples were microscopically analyzed and the results are shown in Table 1.

Results

Figure 2:
FIG. 2 is a photograph of *Bacillus megaterium* ATCC 14581, a Gram positive organism, which has been Gram stained using the three step method of the present invention.

Referring to FIGS. 1 and 2, tests were performed comparing the three reagent Gram staining method of the present invention with the conventional four reagent Gram staining method, applicants found that for certain Bacillus sp., that the subject reagent and method yielded consistent, easily interpreted Gram stain results, while the conventional Gram staining reagents and method yielded inconclusive results. Referring to FIG. 1, the bacteria Gram stained by the traditional four step method appear to be yellowish in color which is inconsistent with the purple color which indicates Gram positive organisms and the pinkish color which indicates Gram negative organisms. However, referring to FIG. 2, the bacteria Gram stained by the three step method of the subject invention are purple in color clearly indicating that the organism is Gram positive.

TABLE 1

| Microorganism | Conventional Four Reagent Gram Staining Method | Three Reagent Gram Staining Method of the Present Invention |
|---|---|---|
| Corynebacterium xerosis ATCC 9016 | g+ | g+ |
| Pseudomonas aeruginosa ATCC 10145 | g− | g− |

TABLE 1-continued

| Microorganism | Conventional Four Reagent Gram Staining Method | Three Reagent Gram Staining Method of the Present Invention |
|---|---|---|
| *Candida albicans* ATCC 10231 | g+ | g+ |
| *Candida tropicalis* ATCC 11307 | g+ | g+ |
| *Staphylococcus aureus* ATCC 25923 | g+ | g+ |
| *Staphylococcus aureus* CDC 2048 | g+ | g+ |
| *Staphylococcus xylosis* ATCC 29971 | g+ | g+ |
| *Micrococcus sp.* IMC 72235 | g+ | g+ |
| *Klebsiella pneumoniae* BMC 3292 | g− | g− |
| *Klebsiella pneumoniae* ATCC 13883 | g− | g− |
| *Klebsiella oxytoca* ATCC 8724-A | g− | g− |
| *Escherichia coli* CDC 313-83 | g− | g− |
| *Bacillus cereus* ATCC 14579 | g+ | g+ |
| *Bacillus megaterium* ATCC 14581 | g+ | g+ |
| *Bacillus subtilis* ATCC 6633 | g+ (purple, brownish) | g+ (all purple) |
| *Bacillus subtilis* ATCC 11774 | g+, g− (brownish) | g+ |

Example 2

Materials and Methods

For the three reagent method of the present invention, clinical samples were affixed to glass microscope slides and were treated with a principal staining solution containing 0.38% crystal violet, 0.44% phenol; a mordant solution containing 10% polyvinylpyrolidone-iodine crystals, 0.66% potassium iodide; and a combination decolorizing and counter-staining solution containing 0.40% safranin, 90% ethanol, and 10% water in a 0.1M acetate buffer, pH 4.5.

Using the three reagent Gram staining method of the present invention, the microorganism samples were: (1) treated with the principal staining solution for 30–60 seconds; (2) rinsed with water; (3) treated with the mordant solution for 30–60 seconds; (4) rinsed with the combination decolorizing and counter-staining solution; (5) treated with the combination decolorizing and counter-staining solution for 20–40 seconds; (6) rinsed with water. Following these steps, the microorganism samples were microscopically analyzed and the results are shown in Table 2.

Results

Tests were performed on clinical samples using the three reagent Gram staining method of the present invention. Applicants found that the three reagent method of the present invention yielded consistent and easily interpreted Gram staining results for a variety of clinically isolated samples. The three reagent method provided accurate, consistent, and easily interpretable results for a variety of typical clinical isolates. These results illustrate the benefits obtained by adjusting the pH of the combination decolorizing and counter-staining solution. Additionally, these results demonstrate the criticality of buffering and acidifying the pH of the combination decolorizing and counter-staining solution in order to stain mammalian cells present in the samples. Without adjusting the pH and buffering the solution, the mammalian cells are not sufficiently differentiable and, therefore, cannot be used to aid in idenfication or diagnosis. Polymorphonuclear leukocytes (PMN's), epithelial cells and similar type cells were easily distinguishable using the Gram staining method of the present invention and aided in the interpretation of the clinical samples.

TABLE 2

| Specimen | Result: 3-Reagent Method |
|---|---|
| Blood A | g+, cocci |
| Blood B | g−, rod; PMN's |
| Blood C | g−, rod |
| Blood D | g+, cocci; PMN's |
| Wound A | g+, cocci; g−, diplococci (bipolar bacilli) |
| Wound B | g+, cocci |
| Sputum A | g+, cocci; g− rods; PMN's |
| Vaginal A | epithelial cells |
| Throat A | g+, coccobacilli, squamous cells |

Example 3

Material and Methods

Samples of microorganisms including bacterial and yeast specimens (see Table 3) were affixed to glass microscope slides and were treated with three reagent Gram staining method of Di Ianni comprised of a principal staining solution containing 1.2 gram crystal violet dye, 2 grams of aniline, and 10% (V/V) of isopropanol in a 100 ml final volume; a combination mordant and decolorizing solution containing 0.66% potassium iodide, 0.33% iodine crystals, and 95% ethanol; and a counter-staining solution containing 1% safranin in an aqueous solution.

Using the three reagent Gram staining method of the Di Ianni '061 patent, microorganism samples were: (1) treated with the principal staining solution for one minute; (2) rinsed with water; (3) treated with the combination mordant and decolorizing solution for one minute; (4) rinsed with water; (5) treated with the counter-staining solution for 30–60 seconds; (6) rinsed with water. Following these steps, the microorganism samples were microscopically analyzed and the results are shown in Table 3.

For the three reagent method of the present invention, identical bacterial specimens were affixed to glass microscope slides and were treated with a principal staining solution containing 0.38% crystal violet, 0.44% phenol; a mordant solution containing 10% polyvinylpyrolidone-iodine crystals, 0.66% potassium iodide; and a combination decolorizing and counter-staining solution containing 0.40% safranin, 90% ethanol, and 10% water in a 0.1M acetate buffer as previously described in Example 1.

Results

Tests were performed comparing the three reagent Gram staining method of the present invention with the three reagent Gram staining method of the Di Ianni '061 patent described above. Applicants found that for organisms from both Gram positive and Gram negative groups, the combination decolorizing and counter-staining reagent and method of the present invention yielded consistent and easily interpreted Gram staining results while the three reagent Gram staining reagent and method of the Di Ianni '061 patent yielded inconclusive and sometimes incorrect results. For example, for *Staphyloccus aureus* ATCC 2048, *Staphyloccus xylosis* ATCC 29971, *Bacillus cereus* ATCC E-14579, *Bacillus megaterium* ATCC 14581, and *Bacillus subtilis* ATCC 11774 the Di Ianni reagent and method yielded either incorrect Gram determinations or inconclusive Gram determinations while the three reagent method of the present invention yielded consistently accurate and easily interpreted results for the same organisms.

TABLE 3

| Microorganism | Di Ianni '061 Three Step Gram Staining Method | Three Step Gram Staining Method of the Present Invention |
|---|---|---|
| *Staphyloccus aureus* ATCC 2048 | g− | g+ |
| *Staphyloccus xylosus* ATCC 29971 | pink-brown | g+ |
| *Bacillus cereus* ATCC E-14579 | g+, g− | g+ |
| *Bacillus megaterium* ATCC 14581 | g+, g− | g+ |
| *Klebsiella pneumoniae* BMC 3292 | g− | g− |
| *Escherichia coli* CDC 313-83 | g− | g− |
| *Bacillus subtilis* ATCC 6633 | g+ | g+ |
| Bacillus subtilis ATCC 11774 | g− | g+ |

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed:

1. A method for Gram staining a specimen containing bacteria by:
   a) staining Gram positive bacteria in the specimen;
   b) fixing the stain to the Gram positive bacteria and;
   c) simultaneously decolorizing and counter-staining Gram negative bacteria in the specimen.

2. The method of claim 1 wherein the Gram negative bacteria are simultaneously decolorized and counter-stained by a solution comprising a decolorizing solvent, a counter-stain, and a buffer.

3. The method of claim 2 wherein said solvent is selected from the group consisting of methanol, ethanol, isopropanol, chloroform, and acetone.

4. The method of claim 3 wherein said solvent comprises ethanol ranging in concentration from 75% to 100%.

5. The method of claim 2 wherein said solvent is 90% ethanol and 10% water.

6. The method of claim 2 wherein said counter-stain comprises safranin in concentrations ranging from 0.25% to 0.8%.

7. The method of claim 6 wherein the concentration of safranin is 0.4%.

8. The method of claim 2 wherein the counter-stain comprises fuchsin in concentrations ranging from 0.02% to 0.2%.

9. The method of claim 8 wherein the concentration of fuchsin is 0.04%.

10. The method of claim 2 wherein said buffer is selected from the group consisting of acetate and TRIS.

11. The method of claim 10 wherein said buffer comprises acetate in concentrations ranging from 0.01M to 1M.

12. The method of claim 11 wherein said buffer is 0.1M acetate.

13. The method of claim 1 further including a step of acidifying mammalian cells contained in the specimen.

14. The method of claim 2 wherein said solution has pH ranging from 1 to 6.

15. The method of claim 14 wherein said solution has a pH of 4.5.

16. A kit for Gram staining containing reagents comprising:
   first reagent means for staining Gram positive bacteria;
   second reagent means for fixing the stain to the Gram positive bacteria; and
   third reagent means for simultaneously decolorizing and de-staining Gram negative bacteria.

17. The Gram staining kit according to claim 16 wherein said third reagent means comprises a solvent a counter-stain, and a buffer.

18. The Gram staining kit according to claim 17 wherein said decolorizing solvent is selected from the group consisting of methanol, ethanol, isopropanol, chloroform, and acetone.

19. The Gram staining kit according to claim 17 wherein said solvent comprises ethanol in concentrations ranging from 75% to 100%.

20. The Gram staining kit according to claim 17 wherein said solvent is 90% ethanol and 10% water.

21. The Gram staining kit according to claim 17 wherein said counter-stain comprises safranin in concentrations ranging from 0.25 to 0.8%.

22. The Gram staining kit according to claim 21 wherein the concentration of safranin is 0.4%.

23. The Gram staining kit according to claim 17 wherein said counter-stain comprises fuchsin in concentrations ranging from 0.02% to 0.2%.

24. The Gram staining kit according to claim 23 wherein the concentration of fuchsin is 0.04%.

25. The Gram staining kit according to claim 17 wherein said buffer is selected from the group consisting of acetate and TRIS.

26. The Gram staining kit according to claim 25 wherein said buffer comprises acetate in concentrations ranging from 0.01M to 1M.

27. The Gram staining kit according to claim 17 wherein said buffer is 0.1M acetate.

28. The Gram staining kit according to claim 17 wherein said solution has pH ranging from 1 to 6.

29. The Gram staining kit according to claim 28 wherein said solution has a pH of 4.5.

30. A Gram staining reagent for simultaneously decolorizing and counter-staining bacteria affixed to a slide consisting of a decolorizing solvent, a counter-stain, and a buffer.

31. The Gram staining reagent of claim 30 wherein said solvent is selected from the group consisting of methanol, ethanol, isopropanol, chloroform, and acetone.

32. The Gram staining reagent according to claim 30 wherein said solvent comprises ethanol in concentrations ranging from 75% to 100%.

33. The Gram staining reagent according to claim 30 wherein said solvent is 90% ethanol and 10% water.

34. The Gram staining reagent according to claim 30 wherein said counter-stain comprises safranin in concentrations ranging from 0.25% to 0.8%.

35. The Gram staining reagent according to claim 34 wherein the concentration of safranin is 0.4%.

36. The Gram staining reagent according to claim 30 wherein said counter-stain comprises fuchsin in concentrations ranging from 0.02% to 0.2%.

37. The Gram staining reagent according to claim 36 wherein the concentration of fuchsin is 0.04%.

38. The Gram staining reagent according to claim 30 wherein said buffer is selected from the group consisting of acetate and TRIS.

39. The Gram staining reagent according to claim 30 wherein said buffer comprises acetate in concentrations ranging from 0.01M to 1M.

40. The Gram staining reagent according to claim 30 wherein said buffer is 0.1M acetate.

41. The Gram staining reagent according to claim 30 wherein said solution has pH ranging from 1 to 6.

42. The Gram staining reagent according to claim 30 wherein said solution has a pH of 4.5.

* * * * *